(12) United States Patent
Dennerlein et al.

(10) Patent No.: US 9,830,685 B2
(45) Date of Patent: Nov. 28, 2017

(54) METHOD FOR THE DETERMINATION OF DUAL ENERGY IMAGE DATA RECORDS AND X-RAY FACILITY

(71) Applicant: SIEMENS AKTIENGESELLSCHAFT, Munich (DE)

(72) Inventors: Frank Dennerlein, Forchheim (DE); Mathias Hoernig, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 196 days.

(21) Appl. No.: 13/966,481

(22) Filed: Aug. 14, 2013

(65) Prior Publication Data

US 2014/0050302 A1    Feb. 20, 2014

(30) Foreign Application Priority Data

Aug. 14, 2012  (DE) .................. 10 2012 214 472

(51) Int. Cl.
    *G06T 5/00*      (2006.01)
    *G06T 11/00*     (2006.01)
    (Continued)

(52) U.S. Cl.
    CPC .............. *G06T 5/001* (2013.01); *A61B 6/482* (2013.01); *G06T 11/005* (2013.01);
    (Continued)

(58) Field of Classification Search
    CPC ......... A61B 6/032; A61B 6/405; A61B 6/482; A61B 6/4035; A61B 6/4241; A61B 6/025;
    (Continued)

(56) References Cited

U.S. PATENT DOCUMENTS 5,661,773 A *  8/1997  Swerdloff et al. .............. 378/65
7,272,429 B2  9/2007  Walker et al.
(Continued)

FOREIGN PATENT DOCUMENTS

DE         10356116 A1    6/2004
DE    102005047420 A1    4/2006
(Continued)

OTHER PUBLICATIONS

Raad et al., Industrial Radiography, Jan. 2007, GE Inspection Technologies, p. 18.*
(Continued)

*Primary Examiner* — Glen Kao
(74) *Attorney, Agent, or Firm* — Laurence Greenberg; Werner Stemer; Ralph Locher

(57) ABSTRACT

A method for determining at least one three-dimensional image data record of a target area from two sets of projection images recorded with x-ray spectra using different energy maxima. A first set of projection images is recorded via a first X-ray spectrum and different first projection directions and a second set of projection images via a second X-ray spectrum and different second projection directions which differ at least partially from the first projection directions. A three-dimensional anatomy image data record is reconstructed from the first and the second projection images. A three-dimensional spectral image data record is reconstructed by a weighted combination of a first three-dimensional reconstruction image data record reconstructed from the first projection images, and a second three-dimensional reconstruction image data record reconstructed from the second projection images. The anatomy image data record and the spectral image data record are displayed.

19 Claims, 2 Drawing Sheets

(51) Int. Cl.
 A61B 6/02 (2006.01)
 A61B 6/00 (2006.01)
 A61B 6/03 (2006.01)
(52) U.S. Cl.
 CPC ............ *G06T 11/006* (2013.01); *A61B 6/025* (2013.01); *A61B 6/03* (2013.01); *G06T 11/008* (2013.01); *G06T 2211/408* (2013.01)
(58) Field of Classification Search
 CPC ....... A61B 6/502; G06T 5/001; G06T 11/006; G06T 2211/408
 USPC ............. 378/5, 4, 8, 9, 21, 38, 62, 131, 901
 See application file for complete search history.

(56) References Cited

U.S. PATENT DOCUMENTS

| | | | | |
|---|---|---|---|---|
| 7,313,216 | B2* | 12/2007 | Nishide | A61B 6/032 378/15 |
| 7,352,885 | B2 | 4/2008 | Eberhard et al. | |
| 7,801,265 | B2 | 9/2010 | Yu et al. | |
| 8,396,275 | B2 | 3/2013 | Bruder et al. | |
| 2003/0108149 | A1* | 6/2003 | Tsuyuki | A61B 6/032 378/54 |
| 2006/0067473 | A1* | 3/2006 | Eberhard et al. | 378/98.9 |
| 2006/0123002 | A1* | 6/2006 | Hornegger | G06T 7/0038 |
| 2007/0133736 | A1* | 6/2007 | Chen | A61B 6/00 378/5 |
| 2007/0189437 | A1* | 8/2007 | Yang et al. | 378/4 |
| 2009/0097611 | A1* | 4/2009 | Nishide et al. | 378/5 |
| 2010/0092060 | A1* | 4/2010 | Bruder et al. | 382/131 |
| 2010/0189212 | A1* | 7/2010 | Zou | 378/5 |
| 2010/0215233 | A1* | 8/2010 | Hsieh | 382/131 |

FOREIGN PATENT DOCUMENTS

| | | |
|---|---|---|
| DE | 102008051043 B3 | 2/2010 |
| WO | WO 2013164725 A1 * 11/2013 | ........... A61B 6/4241 |

OTHER PUBLICATIONS

Wikipedia, "X-ray computed tomography", (Jun. 6, 2012), from the Internet: <<https://web.archive.org/web/20120606093045/http://en.wikipedia.org/wiki/CT_scan>>.*

Schaefer, D., et al., "Motion-Compensated and Gated Cone Beam Filtered Back-Projection for 3-D Rotational X-Ray Angiography", IEEE Transactions on Medical Imaging, Jul. 2006, pp. 898-906, vol. 25, No. 7.

Kolditz, D., et al., "Volume-of-interest (VOI) imaging in C-arm flat-detector CT for high image quality at reduced dose", Medical Physics, May 2010, pp. 2719-2730, vol. 37, No. 6.

Rohkohl, C., "3-D Reconstruction of dynamic high contrast objects for C-Arm CT" Nuclear Science Symposium Conference Record, 2008. NSS '08 IEEE, Oct. 19-25, 2008.

Dennerlein, F., "Cone-beam ROI Reconstruction using the Laplace Operator", 11th International Meeting on Fully Three-dimensional Image Reconstruction in Radiology and Nuclear Medicine, Jul. 11-15, 2011.

* cited by examiner

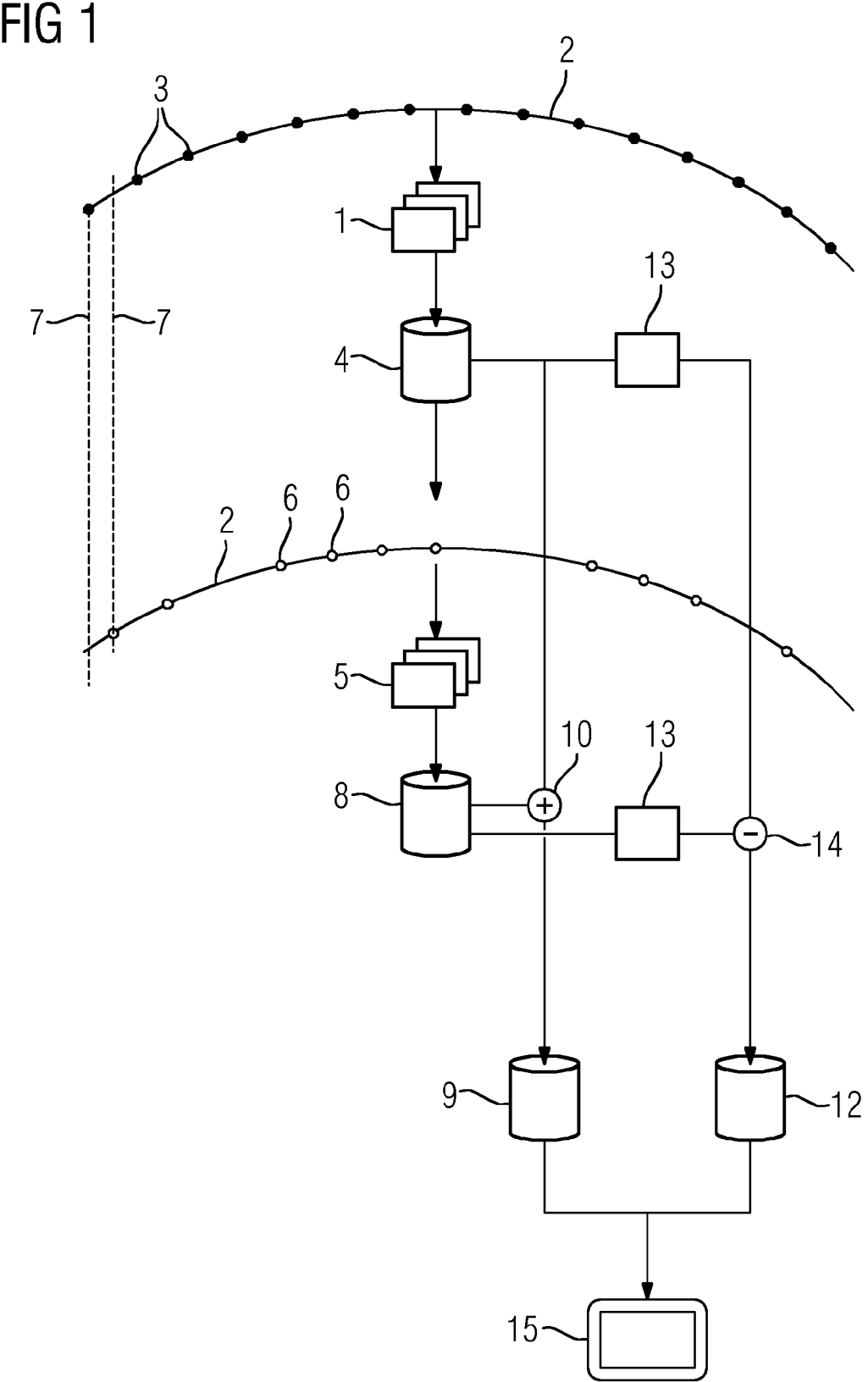

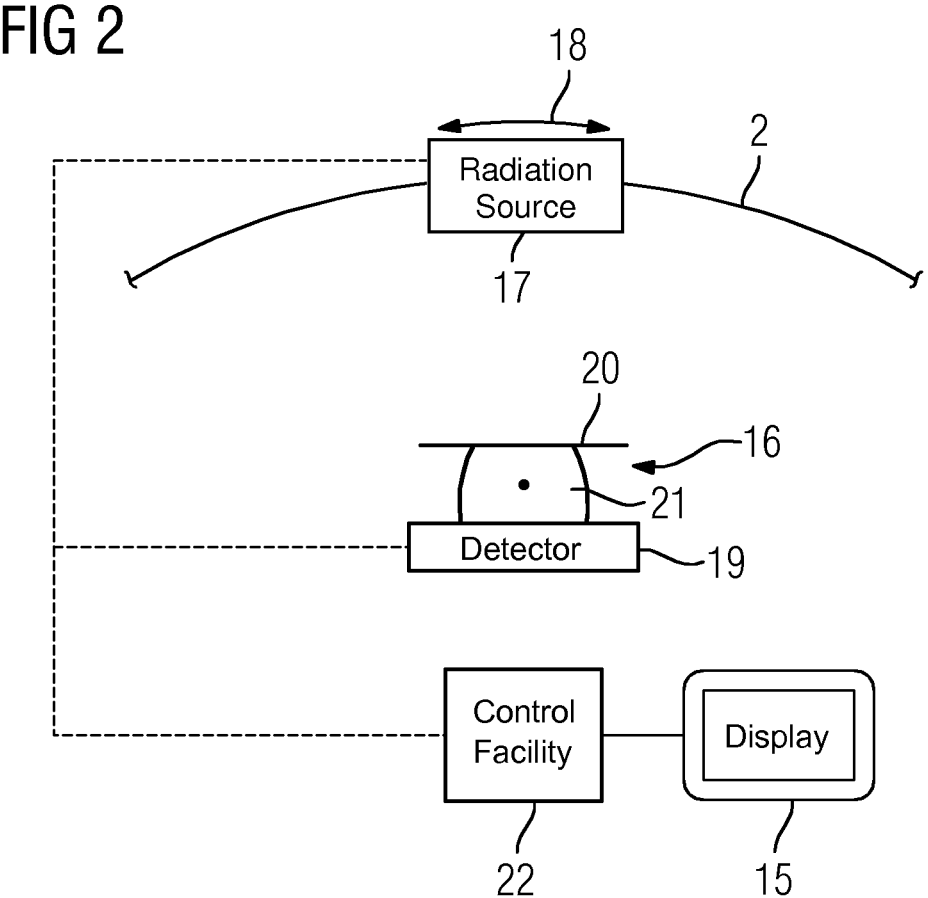

METHOD FOR THE DETERMINATION OF DUAL ENERGY IMAGE DATA RECORDS AND X-RAY FACILITY

CROSS-REFERENCE TO RELATED APPLICATION

This application claims the priority, under 35 U.S.C. §119, of German application DE 10 2012 214 472.2, filed Aug. 14, 2012; the prior application is herewith incorporated by reference in its entirety.

BACKGROUND OF THE INVENTION

Field of the Invention

The invention relates to a method for the determination of at least one three-dimensional image data record of a target area to be displayed from at least two sets of projection images taken with X-ray spectra having different energy maxima. The invention also relates to an X-ray facility.

Recording techniques in which different X-ray energies are used, in specific terms, therefore, X-ray spectra with different energy maxima, in order to create high-energy and low-energy image recordings, are already known in the prior art. They are frequently used in methods which reconstruct three-dimensional image data records from two-dimensional projection images, which are taken from different projection directions, for example by iterative methods or methods of filtered back-projection. Typical areas of application for such dual energy techniques are contrast-enhanced tomosynthesis of the breast or lung, wherein, typically with the prior injection of contrast agent, a low-energy scan followed by a high-energy scan is carried out. Very similar recording techniques are used not only in tomosynthesis imaging, but also in computed tomography, in particular also computed tomography with a C-arm, or generally making use of a flat detector, for example within the framework of a contrast agent-based three-dimensional angiography (DSA) or in order to carry out perfusion measurements.

In many procedures for dual energy recordings it is usual, in this context, to take the second projection images recorded with high energy from the same projection directions as the first projection images. It is therefore possible to carry out a subsequent linear combination of high-energy and low-energy data in the projection space. Accordingly, solutions have been proposed, for example for the tomosynthesis examination of the breast, which include a repetition of the recording trajectory and the projection directions, or a return movement along the recording trajectory, wherein, in turn, second projection images are taken in the same projection directions, in particular projection angles.

Such solutions are disadvantageous in that despite doubling the number of projection images by twice recording projection images, no improvement is achieved in the scanning of the recording trajectory, and therefore also no improvement is possible in aliasing or resolution effects, such as line artifacts, in the reconstructed three-dimensional image data record. A further disadvantage is that despite the achieved movement of scanning positions which have previously already been taken into account, the associated projection directions can often not be exactly reproduced, due to the, in principal, limited precision of the system mechanical arrangement. Methods which rely on the exact reproduction of the recording geometries during the two scan runs are therefore prone to additional image artifacts.

In order to improve the precision of the system, in particular with regard to the reproduction of projection directions (angle precision), a step-and-shoot recording technique has been proposed, this, however, incurs an increase in the recording time, and makes the approach prone to motion artifacts. In addition, this procedure also requires a more elaborate mechanical arrangement.

In three-dimensional digital subtraction angiography imaging with a C-arm X-ray facility, it has been proposed that the data from the two scan runs be algorithmically linked only after a generation of individual reconstruction image data records, for example by back-projection. The assumption of perfect reproducibility of the two scan runs is therefore not valid, with the result that corresponding artifacts can be avoided. Nevertheless, an improvement in scanning along the recording path and an improvement in image quality incurred by this is not possible.

It has also been proposed that a changeover between high-energy and low-energy projections takes place during a single scan run. This however requires significant effort on the part of the radiation source, in particular with regard to preventing a reduction in the service life of an X-ray tube. Additionally, the rapid changeover of the X-ray filter requires a fast and elaborate mechanical arrangement.

SUMMARY OF THE INVENTION

The invention is therefore based on the object of specifying a method, when making recordings of projection images of different energies, in order to generate image data records which reproduce the anatomy and the desired spectral information in high quality.

To achieve the object, with a method of the type referred to in the introduction, according to the invention the following steps are provided:

recording of the first projection images by making use of the first X-ray spectrum and different first projection directions and the second projection images by making use of the second X-ray spectrum and different second projection directions, wherein the second projection directions differ from the first projection directions at least in part and preferably entirely;

reconstructing a three-dimensional anatomy image data record from the first and the second projection images;

reconstructing a three-dimensional spectral image data record by, in particular, weighted combination, in particular subtraction, of a first three-dimensional reconstruction image data record, reconstructed from the first projection images, and a second three-dimensional reconstruction image data record, reconstructed from the second projection images; and displaying the anatomy image data record and the spectral image data record.

It is therefore proposed that fundamentally and deliberately different projection directions, in particular projection angles, be used for the low-energy and high-energy records. This has the advantage that the projection image data from the low-energy recording process will in any event be supplemented by the projection image data from the high-energy recording process, wherein this supplementing is used according to the invention in particular in that a three-dimensional anatomy image data record is based not only, as is already known, on the first projection images, but on both the first and the second projection images, i.e. all projection images. For the anatomy information reproduced by the anatomy data record, this increases the scanning with regard to the anatomy image data record and reduces the artifacts and imprecisions which inevitably already occur, in particular aliasing and line artifacts. According to the invention, provision is therefore not only made for the usual combination of the first reconstruction image data record with the second reconstruction image data record in order to obtain the spectral image data record reproducing the spectral information, but instead the first and the second projection images or, respectively, with a linear reconstruction technique, the first and second reconstruction image data records, are used as the basis for a further image data record, namely the three-dimensional anatomy image data record. In order to represent the soft tissue and/or the morphology, projection images from two scan runs of different energy are therefore used with different projection directions in each case.

The anatomy image data record is therefore produced from all the measured projections, i.e. low-energy and high-energy, for example by making use of an algorithm of the filtered back-projection. The volume which is produced (or, respectively, the layers produced) essentially contains the soft part information, the (entire) morphology, and, for breast diagnostics, the structure of the parenchyma. The high scanning rate along the recording trajectory guarantees a high image quality in the reconstruction, wherein, in particular, line artifacts or aliasing artifacts are effectively avoided.

In addition to the anatomy image data record, naturally a spectral image data record containing the spectral information is also created as a weighted linear combination, preferably a subtraction, of the first reconstruction image data record and of the second reconstruction image data record, i.e. of a low-energy and a high-energy volume. The first reconstruction image data record and/or the second reconstruction image data record can in this situation be produced by iterative reconstruction and/or by the use of a method of filtered back-projection. The spectral image data record essentially contains the additional information conditioned by the spectral energy, for example with regard to a contrast agent, relating to bones, etc.

Provision can be made for the same recording trajectory to be used for the recording of the first and second projection images, wherein the projection directions of the second projection images lie at least partially between projection directions of the first projection images along the recording trajectory. In this way, any "gaps" which are still present in the scanning during the recording of the first projection images can therefore be filled by the second projection images.

Preferably, the number of second projection images recorded during a recording procedure is smaller than the number of first projection images, in particular smaller by a factor. Precisely in terms of the radiation load on a patient, it is expedient if less high-energy projection images, i.e. second projection images, are instead recorded. Methods are also known, however, in which generally several recording procedures for second projection images are carried out, which means that there are several sets of second projection images, which derive from different recording procedures, in particular different movement procedures of the recording trajectory. Provision can then be made for the number of second projection images per recording procedure (scan run) not to be greater than that of the first projection images. It may happen, however, that the total number of second projection images with several temporally staggered recording procedures (scan runs) for second projection images is greater than the total number of first projection images.

The number of second projection images (per recording procedure) can be predetermined by a factor F, for example in accordance with the formula:

$$N(HE)=F*N(LE) \text{ with } F \leq 1.$$

If, in an example, first projection images (low-energy projections) are taken every two angle degrees, therefore, for example, at −25°, −23°, −21°, etc., then, with F=1, provision can be made for the second projection images of a recording procedure to be recorded between the recording positions of the first projection images, i.e. for example at −24°, −22°, −20° etc. It is also conceivable, however, for there to be values of F which are smaller than 1, such that, for example, with F=0.5 it is conceivable for second projection images to be recorded only in every second "gap", therefore, for example, at −22°, −18°, −14°, . . . . For F=0.75 it is conceivable, for example, for second projection images to be recorded at −22°, −20°, −18°, then again at −14°, −12°, −10° etc. In general it can be said that the selection of the projection directions for the second projection images, i.e. in particular the high-energy projection angles, can be predetermined by a logical series, to the projection directions of the first projection images, in particular of the low-energy projection angles.

Provision can however also expediently be made that at least during the examination of a temporally running procedure by means of second projection images taken during at least one recording procedure, in particular the examination of a contrast agent kinetic, the factor is selected in dependence on a time constant of the temporally running procedure, in particular in dependence on an invasion time of a contrast agent. If temporal courses in respect of a contrast agent are to be examined by high-energy recordings, then provision can be made for example for the factor F to be selected in dependence on a time constant of the contrast agent administration, for example by way of the time factor (time from the injection of the contrast agent to the first recording of a second projection image). In this way the contrast agent kinetic can be examined for example.

It is also expedient if the factor is selected in dependence on a requirement of a reconstruction procedure used, in particular as a function of a minimum required number of projection images and/or of a desired signal difference-to-noise ratio. The desired quality, which is subsequently to be available in the reconstruction, can therefore likewise determine how many second projection images are recorded, and therefore the value of the factor F. Accordingly, the factor F can be selected, for example, as a function of the minimum required number of second projection images for the generation of a result volume of a specific quality. It is also conceivable, however, for a minimum or target SdNR of the target area to be shown (SdNR=signal-difference-to-noise-ratio) to be used.

In a particularly advantageous embodiment of the present invention, provision can be made for the selection of the projection directions for the recording of the second projection images to be carried out in dependence on the evaluation of at least one three-dimensional advance recording of the target area and/or of the first reconstruction data record, and/or with at least one further recording procedure of second projection images after a first recording procedure already carried out for second projection images, the selection of the projection directions for the recording of the second projection images is made as a function of the evaluation of the anatomy data record. This finally means that the manner in which "gaps" in the scanning during the recording of the first projection images are filled can also be selected as a function of the object which is to be recorded or, respectively, of the target area. In other words an evaluation of an in particular three-dimensional preliminary recording with regard to possible beam paths can take place. It is preferable, however, if, for example by a real-time computer aided diagnosis (CAD), after their recording, the first projection images or, respectively, the first reconstruction image data record reconstructed herefrom, are evaluated in order to find suitable radiation paths, in particular which are not blocked, among which a recording of further, in this case second, projection images is meaningful. Finally, it is also conceivable if several recording procedures of second projection images take place, therefore several sets of second projection images are recorded, for the anatomy image data record, i.e. a combined high-energy and low-energy reconstruction, to be evaluated accordingly, in order to find suitable projection directions which result in high information gains.

Specifically, provision can be made for the second projection directions to be selected in such a way that significantly weakening beam paths, in particular on account of bones and/or dense tissue, are avoided. In other words, for example, projection angles at which the radiation paths run through dense tissue layers and/or bones are avoided, therefore such radiation paths and such projection directions are preferred in which a lesser weakening takes place, such that with a higher signal strength, structures can be better resolved.

In a further specific embodiment of the present invention, provision can be made for the anatomy image data record to be determined by adding the first and second reconstruction image data record. As has already been mentioned, this is particularly expedient if the first and second reconstruction image data records were determined by a linear reconstruction, since, with the addition of the two reconstruction image data records, effects caused by too small a scanning procedure can be easily calculated. It should also be noted at this point that provision can be made for an energy-dependent weighting of the data of the reconstruction image data records to be carried out. It is therefore conceivable that, in particular already during the reconstruction, making use of an algorithm of the filtered back-projection, an energy-dependent weighting of the data takes place, in order to minimize effects of the different X-ray spectra.

In a further particularly preferred embodiment of the present invention, provision is made that, before the combination of the first and of the second reconstruction image data record to form the spectral image data record, at least one correction algorithm is applied to the reconstruction image data records in order to reduce aliasing or line artifacts. Since in the method according to the invention the linear combination does not take place in the projection space, but instead always in the volume space, it is therefore possible to reduce, in particular, aliasing and/or line artifacts already before the combination to form the spectral image data record, for which conventional methods basically known in the prior art can be used. In this way, this means that by using artifact-reduced reconstruction image data records, the number of artifacts and image interferences in the spectral image data record is also reduced. This becomes apparent as the combination method particularly with subtraction, since with subtraction an enhancement of artifacts can in principle occur.

In a further embodiment of the present invention, for the correction of a movement of the target area, the first projection images can be registered with the second projection images and/or the first reconstruction image data record can be registered with the second reconstruction image data record. In particular when there is a period of time between the recording of the first and second projection images, it is expedient to take account of movements of the target area and to correct them. In this situation, the two reconstruction image data records are registered with one another such that, on the basis of the registration information obtained, patient movements between the scan runs can be compensated for accordingly. The registration information can be used to generate the reconstruction image data records during the back-projection, as is described, for example, in the article by D. Schäfer et al., titled "Motion-Compensated and Gated Cone Beam Filtered Back-Projection for 3-D Rotational X-ray Angiography", IEEE Transactions on Medical Imaging, Vol. 25, Number 7, July 2006, pages 898-906. It is also conceivable, however, for the registration information to be taken into account directly in the linear combination calculation for the spectral image data record and, as appropriate for the anatomy image data record. It is also possible to bring about registration already in the projection image space if one or more projection images of the first and second projection images are indeed recorded with the same projection directions. This means that specific provision can be made for at least one pair of first and second projection images to be recorded with the same projection direction, wherein an item of registration information is determined by a comparison of first and second projection images of the same projection direction.

As has already been explained, provision is made for the anatomy image data record and the spectral image data record to be displayed. This can preferably take place simultaneously. In the clinical workflow, therefore, both image data records, the anatomy image data record and the spectral image data record, are provided, for example, to the doctor preparing the findings, which on the one hand can occur as two individual grey scale images, which can, for example, be displayed next to one another.

It is advantageous, however, if the anatomy image data record and the spectral image data record are merged to form a common display. Provision can therefore be made that two information channels of a single image are used in order to display the two image data records. Provision can therefore be made, for example, that the spectral image data record and the anatomy image data record are displayed in differentiated colors, superimposed on the anatomy image data record or the spectral image data record. Provision can therefore be made for a color coding, in order, for example, to superimpose the information from the spectral image data record onto the anatomy image data record. In this way, excellent identification and evaluation capability by an observer can be achieved.

Aside from the method, the present invention also relates to an X-ray facility, containing a control facility embodied to perform the method according to the invention. Such an X-ray facility can be, for example, a C-arm X-ray facility, with which projection images of the computed tomography type can be recorded from different projection angles, and three-dimensional image data records can be reconstructed. It is also conceivable, however, for the X-ray facility to be embodied as a tomosynthesis X-ray facility, with which, for example, the breast and the lung can be examined. All the citations made regarding the method according to the invention can be transferred by analogy to the X-ray facility according to the invention, with which the same advantages can likewise be attained.

Such an X-ray facility can therefore in particular contain a reconstruction unit for the reconstruction of the anatomy image data record and of the spectral image data record, as well as a display apparatus for displaying the anatomy image data record and the spectral image data record. In addition, a projection direction determination unit can be provided, which determines from which projection directions the second projection images are recorded, which can be carried out in accordance with the variants described. Other components too, which can be realized by hardware and/or software for instance, are conceivable in accordance with the embodiments of the method according to the invention.

Other features which are considered as characteristic for the invention are set forth in the appended claims.

Although the invention is illustrated and described herein as embodied in a method for the determination of dual energy image data records and X-ray facility, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 1 is an illustration showing a performance of a method according to the invention; and FIG. 2 is an illustration of an X-ray facility according to the invention.

DETAILED DESCRIPTION OF THE INVENTION

A method according to the invention is now to be explained in greater detail on the basis of an exemplary embodiment in the field of tomosynthesis. In this situation, a breast is regarded as the target area, wherein, in the first instance, as is usual, the patient data required, such as height, weight, compression thickness and the like are determined. On the basis of the clinical questionnaires, as is usual, basic recording parameters are then determined, such as, for example, the desired number of low-energy and high-energy projection images, the overall angle interval to be covered by the recording trajectory, and gradually along the recording trajectory for the recording of the first projection images, at which the energy maximum of the X-ray spectrum used ("peak energy") is lower than the energy maximum of the X-ray spectrum of the second projection images to be recorded later. Here the projection directions are therefore described by projection angles.

At this starting point the method according to the invention now commences, with which it is intended that two three-dimensional image data sets extremely well-suited for the evaluation should be generated, namely an anatomy image data record and a spectral image data record containing spectral information, which are intended to exhibit a high quality and few artifacts.

As represented in FIG. 1, the method according to the invention begins with a recording of first projection images 1 along a recording trajectory 2, which is shown here diagrammatically with different recording positions 3 (projection angles). For the recording of the first projection images 1 with the X-ray facility, a first X-ray spectrum is used, as already explained, such that low-energy recordings are produced.

From the first projection images 1, a first three-dimensional reconstruction image data record 4 is determined using an algorithm of the filtered back-projection. This is now evaluated in a further step, in order, together with quality requirements for the image data records which are to be finally determined, which form a stipulation for the number of second projection images (high-energy projection images), to determine particularly well-suited projection directions for the second projection images 5 which are now to be recorded. In this situation, as shown in turn on the recording trajectory 2, recording positions 6 are determined, therefore projection angles, which deviate from the recording positions 3 of the first projection images 1, lying specifically between recording positions 3 of the first projection images, as the ancillary lines 7 show. A recording position 6 is also provided, not located at every position between two recording positions 3; fewer second projection images 5 than first projection images 1 are therefore recorded. The projection directions deriving from the recording positions 6 are selected in such a way that less dense tissue and bones need to be irradiated on the resultant radiation paths.

It may be further noted at this point that it is also conceivable, instead of the first reconstruction image data record 4, to make recourse, for example, to a previously recorded image data record of the target area, such as a preliminary recording, and to evaluate this with regard to favorable recording positions 6, therefore projection directions. If several sets of second projection images 5 are recorded in several recording procedures, it is then also conceivable for the anatomy image data record, which is still to be discussed later, to be evaluated correspondingly.

It is essentially also conceivable for the recording positions 6 to be determined in another way, independently of an evaluation described here. For this purpose, second projection images 5, less by a factor or of the same number as first projection images 1 can be recorded, wherein the factor can be derived, for example, from temporal considerations, if, for example, it is intended that a temporally running procedure is to be considered, but can also be derived from quality considerations, for example from a number of second projection images 5, which are required for a sufficiently higher quality reconstruction, and the like. The recording positions 6 can then be selected in such a way that they are connected by a logical series with the recording positions 3.

From the second projection images 5, in turn by way of a method of filtered back-projection, a second three-dimensional reconstruction image data record 8 is then reconstructed.

The reconstruction image data records 4, 8 are now used in order to generate two image data records to be displayed later and which can be used for the evaluation. One anatomy image data record 9, clearly showing the anatomy on the basis of the accrued good scanning along the recording trajectory 2 is generated by straightforward addition, Operation 10, from the first reconstruction image data record 4 and the second reconstruction image data record 8. Artifacts which occur as a result of too little scanning are in this way at least partially calculated. Provision can optionally be made for a weighting to be applied, as a function of the energy, and finally the energy maximum, of the respective X-ray spectrum.

In order to determine the spectral image data record 12 containing the spectral information obtained by using different X-ray spectra, in the first instance, as indicated by the boxes 13, the reconstruction image data records 4, 8 are subjected to a correction algorithm for the reduction of aliasing and/or line artifacts. Once the aliasing and/or line artifacts have been reduced, a subtraction (if appropriate, in turn weighted) takes place of the thus corrected reconstruction image data records 4, 8, Operation 14. The result is the spectral image data record 12.

It may also be noted at this point that with this exemplary embodiment it was assumed that between the recording of the first projection images 1 and the second projection images 5 no movement of the target area took place, i.e. no movement correction was required. Such a movement can, however, be taken into account within the framework of the present invention, for example in that the first and the second reconstruction image data record 4, 8 are registered with one another, in order to be able to obtain registration information and to carry out an appropriate correction. Provision may also be made for specifically at least one pair formed from a first projection image 1 and a second projection image 5 nevertheless to be recorded at the same recording position 3, 6, therefore using the same projection direction, such that these projection images, in each case as a pair, can likewise be compared in order to obtain registration information, which can then already be taken into account in the reconstruction of the reconstruction image data records 4, 8 in order to carry out the movement correction.

In a last step of the method according to the invention, the anatomy image data record 9 and the spectral image data record 12 are merged, in order to be represented jointly on a display apparatus 15. To this end, provision is made to integrate the spectral image data record 12 by a color coding into the anatomy image data record 9, such that a simple and intuitive acquisition capability is derived. As an alternative it is also conceivable for representations of both image data records 9, 12 to be displayed and the like jointly as grey scale images.

FIG. 2 finally shows a basic diagram of an X-ray facility 16 according to the invention, which in this case is realized as a tomosynthesis X-ray facility 16. A radiation source 17, with which the two X-ray spectra can be generated, as indicated by the arrow 18, can be moved along the recording trajectory 2 guided by an appropriate mechanical arrangement. X-ray radiation emitted from the radiation source 17 is received in every position of the radiation source 17 by a flat detector 19, which is fixed. A compression plate 20 can be allocated to the X-ray detector 19, in order for the target area, for example a breast 21, to be compressed for the recording.

The operation of the X-ray facility 16 is controlled by a control facility 22, which is designed for the performance of the method according to the invention. This means that the control facility 22 actuates the recording arrangement, consisting of the radiation source 17 and X-ray detector 19 in the appropriate manner in order to record first and second projection images 1, 5 along the recording trajectory 2. A reconstruction unit of the control facility 22 allows for the reconstruction of the corresponding image data records, wherein the image data records 9, 12 can be represented on the display facility 15 allocated to the X-ray facility 16.

Although the invention has been illustrated and described in detail by the preferred exemplary embodiment, the invention is nevertheless not restricted by the disclosed examples, and other variations can be derived by the person skilled in the art without departing from the scope of protection of the invention.

The invention claimed is:

1. A method for determining at least one three-dimensional image data record of a target area to be displayed from at least two sets of projection images recorded with x-ray spectra having different energy maxima, which comprises the steps of:
   recording first projection images via a first X-ray spectrum and different first projection directions;
   recording second projection images via a second X-ray spectrum and different second projection directions, wherein the second projection directions differ at least partially from the first projection directions;
   reconstructing a three-dimensional anatomy image data record from the first and the second projection images;
   reconstructing a three-dimensional spectral image data record by means of a weighted combination of a first three-dimensional reconstruction image data record, reconstructed from the first projection images, and a second three-dimensional reconstruction image data record, reconstructed from the second projection images; and
   displaying the three-dimensional anatomy image data record and the spectral image data record;
   wherein a total number of the second projection images recorded during a completed recording procedure is smaller than a total number of the first projection images recorded during a completed recording procedure, and wherein the second projection images are taken with a higher energy than the first projection images.

2. The method according to claim 1, wherein for the recording of the first and the second projection images, using a same recording trajectory, the second projection directions of the second projection images lie at least partially between the first projection directions of the first projection images along the same recording trajectory.

3. The method according to claim 1, wherein at least during an examination of a temporally running procedure by means of the second projection images recorded during at least one recording procedure, selecting a factor by at least one of:
   selecting the factor in dependence on a time constant of a temporally running procedure; or
   selecting the factor in dependence on a requirement of a reconstruction method used.

4. The method according to claim 1, which further comprises:
   making a selection of the different second projection directions for the recording of the second projection images in dependence on at least one of:
      an evaluation of at least one three-dimensional preliminary recording of a target area;
      the first three-dimensional reconstruction data record; or
      at least one further recording procedure of the second projection images after an already effected first recording procedure for the second projection images, a selection of the different second projection directions for the recording of the second projection images of the further recording procedure is effected in dependence on an evaluation of the three-dimensional anatomy data record.

5. The method according to claim 4, which further comprises selecting the different second projection directions in such a way that significantly weakening radiation paths, including due to bone or dense tissue, are avoided.

6. The method according to claim 1, which further comprises determining the three-dimensional anatomy image data record by adding the first and the second reconstruction image data records.

7. The method according to claim 6, which further comprises carrying out an energy-dependent weighting of data of the first and second three-dimensional reconstruction image data records.

8. The method according to claim 1, wherein from a combination of the first and the second reconstruction image data records forming the three-dimensional spectral image data record, at least one correction algorithm for at least one of reducing aliasing or line artifacts is applied to the first and second three-dimensional reconstruction image data records.

9. The method according to claim 1, wherein for a correction of a movement of the target area, performing at least one of:
registering the first projection images with the second projection images; and
registering the first three-dimensional reconstruction image data record with the second three-dimensional reconstruction image data record.

10. The method according to claim 9, which further comprises recording at least one pair of first and second projection images in a same projection direction, wherein an item of registration information is determined by comparison of the first and second projection images from the same projection direction.

11. The method according to claim 1, which further comprises merging the three-dimensional anatomy image data record and the three-dimensional spectral image data record for joint display.

12. The method according to claim 11, which further comprises displaying an image obtained by superimposing the three-dimensional spectral image data record on the three-dimensional anatomy image data record with color differentiation or by superimposing the three-dimensional anatomy image data record on the three-dimensional spectral image data record with color differentiation.

13. The method according to claim 1, wherein:
the second projection directions differ wholly from the first projection directions; and
the three-dimensional spectral image data record is reconstructed by subtraction.

14. The method according to claim 1, wherein at least during an examination of a contrast agent kinetic procedure by means of the second projection images recorded during at least one recording procedure, performing at least one of:
selecting a factor in dependence on an invasion time of a contrast agent; or
selecting the factor in dependence on at least one of a minimum number of projection images required or a desired signal difference-to-noise ratio.

15. The method according to claim 1, wherein the three-dimensional anatomy image data record and the three-dimensional spectral image data record are merged and simultaneously displayed.

16. The method according to claim 1, wherein the total number of the second projection images is equal to or less than a factor times the total number of the first projection images and the factor is 0.75.

17. An X-ray facility, comprising:
a control facility programmed to perform a method for determining at least one three-dimensional image data record of a target area to be displayed from at least two sets of projection images recorded with x-ray spectra having different energy maxima, which comprises the steps of:
recording first projection images via a first X-ray spectrum and different first projection directions;
recording second projection images via a second X-ray spectrum and different second projection directions, wherein the second projection directions differ at least partially from the first projection directions;
reconstructing a three-dimensional anatomy image data record from the first and the second projection images;
reconstructing a three-dimensional spectral image data record by means of a weighted combination of a first three-dimensional reconstruction image data record, reconstructed from the first projection images, and a second three-dimensional reconstruction image data record, reconstructed from the second projection images; and
displaying the three-dimensional anatomy image data record and the three-dimensional spectral image data record;
wherein a total number of the second projection images recorded during a completed recording procedure is smaller than a total number of the first projection images recorded during a completed recording procedure, and wherein the second projection images are taken with a higher energy than the first projection images.

18. The X-ray facility according to claim 17, wherein the three-dimensional anatomy image data record and the three-dimensional spectral image data record are merged and simultaneously displayed.

19. The X-ray facility according to claim 17, wherein the total number of the second projection images is equal to or less than a factor times the total number of the first projection images and the factor is 0.75.

* * * * *